US012616651B2

(12) United States Patent
Modi

(10) Patent No.: US 12,616,651 B2
(45) Date of Patent: May 5, 2026

(54) TOPICAL LIPOLYSIS COMPOSITION AND METHODS

(71) Applicant: Lipodissolve Therapeutics Inc., Ancaster (CA)

(72) Inventor: Pankaj Modi, Ancaster (CA)

(73) Assignee: Lipodissolve Therapeutics Inc., Ancaster (CA)

( * ) Notice: Subject to any disclaimer, the term of this patent is extended or adjusted under 35 U.S.C. 154(b) by 1159 days.

(21) Appl. No.: 17/496,685

(22) Filed: Oct. 7, 2021

(65) Prior Publication Data

US 2022/0047499 A1 Feb. 17, 2022

Related U.S. Application Data

(63) Continuation-in-part of application No. 15/052,157, filed on Feb. 24, 2016, now abandoned, which is a
(Continued)

(51) Int. Cl.
*A61K 31/685* (2006.01)
*A61K 9/00* (2006.01)
(Continued)

(52) U.S. Cl.
CPC .......... *A61K 9/0014* (2013.01); *A61K 9/1682* (2013.01); *A61K 31/575* (2013.01);
(Continued)

(58) Field of Classification Search
CPC .. A61K 9/0014; A61K 9/1682; A61K 31/575; A61K 31/685; A61K 41/0047; A61K 45/06
See application file for complete search history.

(56) References Cited

U.S. PATENT DOCUMENTS 5,891,083 A 4/1999 Capella et al.
6,663,885 B1 12/2003 Hager et al.
(Continued)

FOREIGN PATENT DOCUMENTS

CA 2229286 8/1999
CA 2354148 6/2000
(Continued)

OTHER PUBLICATIONS

Al Faresi, Fatima, and Hassan I. Galadari. "Mesotherapy: myth and reality." Expert Review of Dermatology 6.2 (2011): 157-162. (Year: 2011).*

(Continued)

*Primary Examiner* — James H Alstrum-Acevedo
*Assistant Examiner* — Justin Christopher Sanchez
(74) *Attorney, Agent, or Firm* — Gowling WLG (Canada) LLP

(57) ABSTRACT

A method for non-surgically reducing localized adipose tissue in a patient is provided. The method comprises topically administering to a site at or proximate adipose tissue, with massage at the site of administration, a composition comprising: at least one biologically compatible pharmacologically active detergent selected from the group consisting of a lipophilic detergent, a hydrophilic detergent, an ionic detergent, a non-ionic detergent, a zwitterionic detergent, a glyceride and a bile acid or salt thereof in a concentration ranging from about 0.5% to about 30% by wt of the composition and at least one phospholipid. In one embodiment, a novel composition comprising deoxycholic acid or a salt thereof at a concentration ranging from about 0.5% to about 30% by wt, and phosphatidylcholine at a concentration ranging from about 0.1% to about 2% by wt, in a cream base is also provided.

11 Claims, 4 Drawing Sheets

A
Before

B
After 30 days

C
Skin Penetration Data

Related U.S. Application Data continuation of application No. 14/549,732, filed on Nov. 21, 2014, now abandoned.

(51) Int. Cl.

| | |
|---|---|
| *A61K 9/16* | (2006.01) |
| *A61K 31/575* | (2006.01) |
| *A61K 41/00* | (2020.01) |
| *A61K 45/06* | (2006.01) |

(52) U.S. Cl.
CPC ........ *A61K 31/685* (2013.01); *A61K 41/0047* (2013.01); *A61K 45/06* (2013.01)

(56) References Cited

U.S. PATENT DOCUMENTS

| | | | |
|---|---|---|---|
| 7,914,469 B2 | 3/2011 | Torbati | |
| 2005/0089555 A1 | 4/2005 | Boderke et al. | |
| 2005/0143347 A1 | 6/2005 | Boderke et al. | |
| 2005/0158408 A1 | 7/2005 | Yoo | |
| 2005/0261258 A1 | 11/2005 | Kolodney et al. | |
| 2005/0267080 A1 | 12/2005 | Kolodney et al. | |
| 2005/0287199 A1 | 12/2005 | Denney et al. | |
| 2006/0074057 A1 | 4/2006 | Marchewitz | |
| 2006/0127468 A1 | 6/2006 | Kolodney et al. | |
| 2006/0154906 A1 | 7/2006 | Kolodney et al. | |
| 2006/0222673 A1 | 10/2006 | Chern et al. | |
| 2008/0058287 A1* | 3/2008 | Rose ...................... | A61P 43/00 514/109 |
| 2009/0275545 A1 | 11/2009 | Boderke et al. | |
| 2011/0082124 A1 | 4/2011 | Burkhart et al. | |
| 2012/0201857 A1* | 8/2012 | Modi ..................... | A61K 39/08 977/788 |
| 2012/0237492 A1 | 9/2012 | Webster | |
| 2012/0258943 A1 | 10/2012 | Hodge et al. | |
| 2013/0190282 A1 | 7/2013 | Hodge et al. | |

FOREIGN PATENT DOCUMENTS

| | | |
|---|---|---|
| CA | 2382535 | 3/2001 |
| CA | 2543187 | 5/2005 |
| CA | 2551474 | 7/2005 |
| CA | 2567298 | 12/2005 |
| CA | 2789109 | 12/2008 |
| WO | 2005112942 | 12/2005 |
| WO | 2005117900 | 12/2005 |

OTHER PUBLICATIONS

Burnett, Christina L., et al. "Final report of the safety assessment of kojic acid as used in cosmetics." International journal of toxicology 29.6_suppl (2010): 244S-273S. (Year: 2010).*

Fiume, Monice M., et al. "Final report of the cosmetic ingredient review expert panel on the safety assessment of dicarboxylic acids, salts, and esters." International journal of toxicology 31.4_suppl (2012): 5S-76S. (Year: 2012).*

Ramos-e-Silva, Marcia, et al. "Oleoma: rare complication of mesotherapy for cellulite." International journal of dermatology 51.2 (2012). (Year: 2012).*

Chang, Rong-Kun, et al. "Generic development of topical dermatologic products: formulation development, process development, and testing of topical dermatologic products." The AAPS journal 15.1 (2013): 41-52. (Year: 2013).*

Rotunda et al.—Detergent Effects of Sodium Deoxycholate are a Major Feature of an Injectable Phosphatidylcholine Formulation used for Localized Fat Dissolution, Dermatol Surg. 30 (2004) 1001-1008.

Bechara et al.—Fat tissue after lipolysis of lipomas: a histopathological and immunohistochemical study, J Cutan Pathol 34 (2007) 552-557.

Rose and Morgan—Historical changes associated with mesotherapy, J Cosmet Laser Ther 7 (2005) 17-19.

Lee and Chang—Subcutaneous nodules showing fat necrosis owing to mesotherapy, Dermatol Surg 31 (2005) 250-251.

Caruso et al.—An evaluation of Mesotherapy solutions for inducing lipolysis and treating cellulite, J Plast Reconstr Aesthet Surg 61 (2008) 1321-1324.

Rotunda et al.—Lipomas treated with subcutaneous deoxycholate injections, J am Acad Dermatorl, vol. 53, No. 6, 2005, pp. 973-978.

Miller et al.—"Overview of Therapeutic Ultrasound Applications and Safety Considerations", J Ultrasound Med 2012; 31(4): 623-634.

* cited by examiner

A

Before

B

After 30 days

C

Skin Penetration Data

A

Before : Placebo

B

After 6 weeks: Placebo

C
Before: Treated

D
After 6 weeks: Treated

A

B

C

D

E

F

G

H

A

B

C

D

TOPICAL LIPOLYSIS COMPOSITION AND METHODS

Pharmacologically active compositions and methods using the compositions for topical, i.e., non-surgical administration to patients in need thereof with demonstrated efficacy in reducing or removing localized adipose tissue, i.e., a deposit of fat cells including but not limited to lipomas. In one embodiment, administration is by application to a skin surface at or proximate to a localized adipose tissue site. In one embodiment, administration is subcutaneous at or proximate to localized adipose tissue. In one embodiment, administration is percutaneous, i.e., absorption through the skin from topical application at or proximate to localized adipose tissue. Percutaneous administration may be directly to a skin surface, i.e., to the skin itself, or indirectly, e.g., to a surface such as a pad that then contacts the skin. All such administration methods are topical administration.

The method results in clinically demonstrated decreased localized deposits of adipose tissue, i.e., fat, for cosmetic improvement. Exemplary uses include but are not limited to therapy for lower eyelid fat herniation, on the neck, under the chin, lipodystrophy, and fat deposits associated with cellulite. The compositions are provided into or proximal to adipose tissues after penetration of the superficial skin layers into subcutaneous layers. The compositions include detergents and can also include other agents such as anti-inflammatory agents, analgesics, dispersion or anti-dispersion agents and pharmaceutically acceptable excipients and drugs of high or low molecular weight.

There is increased prevalence of both surgical and non-surgical procedures for improving appearance with a population that is aging and gaining weight. Liposuction, also known as lipoplasty or suction lipectomy, is a popular procedure that removes fat through an incision in the skin through which a cannula is inserted, optionally with solutions to assist the process. The cannula is connected to a suction source and the fat is aspirated through the cannula and discarded. Liposuction is performed under general or local anesthesia, depending on the amount and location of the fat to be removed. It is an expensive and painful procedure.

The most commonly used forms of liposuction additionally use fluid injection methodologies where a medicated solution of a mixture of salts, an anesthetic, and a vasoconstrictor is infused into the treatment site prior to fat aspiration. The medicated solution helps the fat be removed more easily, reduces blood loss, and provides anesthesia both during and after surgery.

However, liposuction and other surgical methods of fat removal are associated with significant adverse events. These include bruising, swelling, numbness, soreness, burning sensation, risk of infection, pigmentation changes, formation of fat clots or blood clots that can migrate to the lungs and can cause death, excessive fluid loss leading to shock or fluid accumulation that must be drained, friction burns or other damage to the skin or nerves, or perforation of vital organs. Liposuction requires a recovery time of one to two weeks where the patient cannot work or perform certain daily activities. Because liposuction requires local and occasionally general anesthesia, there are significant anesthesia-related risks. Such surgical procedures are expensive, time consuming, very painful, require hospitalization, and can led to serious side effects and scars if performed improperly.

Formulations containing phosphatidyicholine and bile salts (PBFs) are used to treat localized fat accumulation. Open label clinical studies reported promising results using PBF injections for treatment of localized fat accumulation, including lower eyelid fat herniation and "buffalo hump" lipodystrophy, cellulites, etc. Phosphatidylcholine (PPC) is a natural phospholipid that is an essential component of normal cell membranes and is important for cell membrane repair. Phosphatidylcholine is also the major delivery form of the essential nutrient choline. Choline is a precursor in the synthesis of the neurotransmitter acetylcholine, the methyl donor betaine and phospholipids, including phosphatidylcholine and sphingomyelin among others. Phosphatidylcholine is also involved in the hepatic export of very-low-density lipoproteins.

Bile salts have been used to improve the aqueous solubility of phosphatidylcholine and more recently medications like amphotericin B, Taxol®, diazepam, antipain medications, anti-inflammatory drugs, several anticancer and anti-tumor compounds, some proteins such as insulin, heparin, neurotoxins, vaccines, etc.

In one embodiment the inventive composition with demonstrated clinical efficacy combines highly purified phosphatidylcholine with the secondary bile salt sodium deoxycholate, an antimicrobial, alcohol, and water to form a stable mixed micelle preparation that can be rapidly sterilized and used for topical administration. Pharmaceutical preparations of this composition can be marketed for treatment of liver disease and hyperlipidemia, respectively, when infused intravenously.

Phosphatidylcholine formulations that are injected are associated with localized burning sensations, erythema, transient urticaria, and variable degrees of pruritus, as well as sequelae of ulceration and pain. An infectious granulomatous reaction was reported in the thigh of a patient at the site of multiple phosphatidyicholine injections. Increased dosages of injected phosphatidylcholine have paralleled side effects seen with large doses of oral and intravenous formulations and include nausea, diarrhea, abdominal pain, and syncope.

The mechanism whereby phosphatidyicholine-containing formulations causes reduction of subcutaneous fat deposits is unknown. Without being limited to a single theory, phosphatidyicholine could reduce the size of lipocytes by stimulating lipase activity. Alternatively, PBFs may function as a detergent that emulsifies lipocyte cell membranes. Detergents have been used in medicine for decades, specifically, as sclerosing agents in sclerotherapy. Detergents possess unique polar and non-polar chemical properties that facilitate emulsification of insoluble substances by reducing surface tension at their interface.

Numerous topical and nontopical treatments are currently available to treat localized adiposities and lipodystrophies. Some treatments are scientifically based, some are pseudo-scientifically empirically based. Notably, prior to the disclosed invention, only injections, i.e., invasive methods, achieved clinically satisfactory results. All topical methods either were not proven effective or their reported use did not demonstrate clinical efficacy.

Capella U.S. Pat. No. 5,891,083 provides an example of adjuvant solutions for liposuction with a carrier solution. One embodiment discloses the compound is an enzyme, particularly lipase or colipase. The enzyme is added to a carrier such as saline solution to provide a lipolysis solution. Another embodiment discloses emulsifying agents such as bile salts may be beneficial in combination or as the primary active compound added to the solution. In all embodiments, the lipolysis solution is administered for a period of time before liposuction to allow the solution to infiltrate the fat tissue. Nowhere is use of a lipolysis solution alone disclosed as a non-surgical means for removing fat from the body. In all examples and embodiments, liposuction is used as a surgical procedure for fat removal and lipase and bile salts are provided as an adjuvant to liposuction.

U.S. Patent Application Publication No. 2013/0190282 discloses an aqueous pharmaceutical formulation comprising less than about 5% whe sodium deoxycholate maintained at a pH sufficient to substantially inhibit precipitation of the sodium deoxycholate. It also discloses methods to inhibit precipitation of sodium deoxycholate in an aqueous solution comprising less than about 5% w/v of sodium deoxycholate, by maintaining the solution pH at 8.0 to about 8.5. The formulation is suitable for injection into a human. One embodiment is an aqueous pharmaceutical formulation comprising less than about 5% wiv sodium deoxycholate in water maintained at a pH of about 8.3.

U.S. Patent Application Publication No. 201210237492 discloses non-surgical reduction of localized subcutaneous fat, such as that associated with cosmetic fat accumulation in the submental area, particularly under the chin. The methods uses compositions having specific concentrations of a salt of deoxycholic acid that provides fat cell necrosis with modest adverse effects. Subrnental fat is reduced by a plurality of subcutaneous injections of a solution of deoxycholic acid or a salt thereof into the submental fat, each injection administering about 0.1 mg to about 0.2 mg of deoxycholic acid or salt thereof per square centimeter of the skin area over the submental fat.

U.S. Patent Application Publication No. 2012/0258943 discloses an aqueous pharmaceutical composition comprising about 0.4% w/v to less than about 2% v√/v of a salt of deoxycholic acid, the composition maintained at pH 8.1 to about 8.5 such that the composition is stabilized against precipitation. Methods for stabilizing the composition by maintaining pH of the solution from about 8.1 to about 8.5 are disclosed.

The bile acid deoxycholic add is reported to have fat removing properties when injected into fatty deposits in vivo ('NO 2005/117900, WO 2005/112942, U.S. Nos. 2005/0261258, 2005/0267080. 2006/127468, and 2006/0154906). Deoxycholate injected into fat tissue has the effects of degrading fat cells via a cytolytic mechanism and causing skin tightening. Both of these effects are required to mediate the desired aesthetic corrections i.e., body contouring. The effects of deoxychcAate into fat are spatially contained because once injected deoxycholate is rapidly inactivated by exposure to protein, e.g. albumin, and then rapidly returns to the intestinal contents. As a result of this attenuation effect that confers clinical safety, fat removal therapies typically require 4-6 sessions. This localized fat removal without surgery is beneficial not only for therapeutic treatment relating to pathological localized fat deposits (e.g., dyslipidemias incident to medical intervention in 11 W treatment), but also for cosmetic fat removal without the attendant inherent surgical risks (e.g., liposuction) (Rotunda et al., Dermatol, Surgery "Detergent effects of sodium deoxycholate are a major feature of an injectable phosphatidyicholine formulation used for localized fat dissolution', 2004, 30: 1001-1008; and Rotunda et al., J. Am. Acad. Dermatol. "Lipomas treated with subcutaneous deoxycholate injections", 2005: 973-978).

U.S. Patent Application Publication No. 20110082124 discloses treating a lipoma by contact with a detergent by deep intramuscular injections to dissolve the lipoma. The detergent may be a cholate, deoxycholate or similar detergent.

Boderke U.S. Patent Application Publication No. 2009/0275545 discloses injecting aqueous phospholipid systems comprising at least one phospholipid, at least one bile acid and water for treating adipose tissue disorders, leading to regression of pathologically proliferated adipose tissue.

U.S. Patent Application Publication No. 20060222673 discloses viscous injectable phosphatidyicholine preparations and their use for reduction or removal of localized adipose tissue (fat) deposits, and to intra-fat pad injection and implant methods of administering by injections for non-surgical removal or reduction of localized fatty deposits.

U.S. Patent Application Publication No. 2006/0154906 discloses non-surgical removal of localized fat deposits using injectable pharmacologically active detergents that lack phosphatidylcholine. The compositions are used for treating localized accumulations of fat including lower eyelid fat herniation, lipodystrophy and fat deposits associated with cellulite and require surgical procedures such as liposuction.

U.S. Patent Application Publication No. 2006/0074057 discloses use of chenodeoxycholic acid to reduce adipose tissue and thereby reduce weight in mammals. The chenodeoxycholic acid is injected or orally administered (tablet, pill, capsule or liquid suspension).

U.S. Patent Application Publication No. 2005/0287199 discloses removal of subcutaneous fat deposits in a human using a lecithin based biphasic injection dosage formulation. It is applicable to subcutaneous, intramuscular and intravenous administration. It also discloses a program based treatment approach by injections of this formulation, application of compression garments, diet modification, and exercise. The formulation comprises an adjustable buffer, an antioxidant, and a stabilizer, and includes liposomes with components that are therapeutic in the treatment of several human ailments. It is also presumed to be efficacious in treating striae albicantes, striae atrophicae, cellulite, and decreased skin turgor.

U.S. Patent Application Publication No. 2005/0158408 discloses pharmaceutical compositions comprising clear aqueous injectable solutions of bile acids that do not form any detectable precipitates over selected pH ranges. The compositions may comprise water, a bile acid in the form of a bile acid, bile acid salt, or a bile acid conjugated with an amine by an amide linkage, and either or both an aqueous soluble starch conversion product and an aqueous soluble non-starch polysaccharide. The composition, in embodiments, may further contain a pharmaceutical compound in a pharmaceutically effective amount. The disclosure further provides dried forms of primary aqueous solubilized bile acid formulations and methods of preparing the dried forms.

U.S. Patent Application Publication No. 2005/0143347 discloses aqueous injection preparations comprising at least one phospholipid or bile acid and a component assisting degradation of fat such as riboflavin and water are suitable for producing medicaments for removing subcutaneous accumulations of fat and lead to regression of diet-resistant fat pads.

U.S. Patent Application Publication No. 2005/0089555 discloses aqueous phospholipid systems comprising at least one phospholipid, at least one bile acid and water. These produce medicaments for treatment of adipose tissue disorders and lead to regression of the pathologically proliferated adipose tissue using injections.

U.S. Pat. No. 6,663,885 discloses an injectable aqueous liposome system comprising at least one phospholipid, a non-phospholipidic substance which is a bile acid or derivative, and optionally a non-toxic organic solvent. The mass ratio of phospholipid to the non-pholipidic substance ranges between 1:0.001 and 1:0.1.

Injection treatments are painful, expensive, and require long healing time and multiple treatments to achieve the desired outcome. A desirable method removes localized fat accumulations without surgery, without painful multiple injections, and without prolonged recovery time, and with fewer adverse side effects than currently available methods.

The inventive composition is clinically proven to reduce unwanted adipose tissue at or proximate to the administration area. It provides lipo-dissolving agents in a formulation for topical application such as a cream, lotion, emulsion, paste, ointment, etc. Prior to the invention topical treatments using transdermal delivery methods other than percutaneous injections had the highest failure rate because only a very small percentage, if any, of a lipo-dissolving cream, ointment, lotion, etc. could penetrate the nearly impermeable horny stratum corneum layer of skin.

Without being limited to a specific theory, a possible mechanism of action is the detergent action of deoxycholate non-specifically inducing fat cell destruction. Human fat injected with a compounded phosphatidylcholine formulations (PC/DC) results acutely adipocyte vacuolization and in acute and chronic inflammation within the septae and lobules of the subcutaneous fat. Recruited inflammatory cells directly disrupt or indirectly destroy the adipocyte cell membranes via cytokine or lytic enzyme release, resulting in eventual fat necrosis. The inflammatory response may abate with fibrocyte ingrowth and collagen production (Bechara et al. (2007) Fat tissue after lipolysis of lipomas: a histopathological and immunohistochemical study. J Cutan Pathol 34: 552-557; Rose and Morgan (2005) Histological changes associated with mesotherapy for fat dissolution. J Cosmet Laser Ther 7: 17-19; Lee and Chang (2005) Subcutaneous nodules showing fat necrosis owing to mesotherapy. Dermatol Surg 31: 250-251; 4 Caruso et al. (2007) An evaluation of mesotherapy solutions for inducing lipolysis and treating cellulite. J Plast Reconstr Aesthet Surg October 20. doi:10.1016/j.bjps.2007.03.039).

Combinations of lipolytic stimulators, such as melilotus, aminophylline, yohimbine, and isoproterenol, stimulate lipolysis more than each of the individual components alone. Although lidocaine and other topical anesthetics inhibit lipolysis, it is believed that local anesthetics, such as lidocaine and its class derivatives, should not be used in combination with mesotherapy solutions designed to cause local fat reduction or to reduce the appearance of cellulite.

The exact mechanism of action of phosphatidylcholine in subcutaneous tissue is not clear. Theories include its action as an emulsifying/tenso active agent making lipids water soluble, its stimulation of fat splitting lipases activity and release so that triglycerides are hydrolyzed into fatty acids and glycerol, its stimulation of 13-receptors or its inhibition of a2-receptors, thus increasing lipolysis activity and accelerating fat elimination through the gastrointestinal and urinary systems.

The invention provides methods and formulations for demonstrated reductions in subcutaneous fat deposits non-invasively, i.e., topically. A topical formulation was applied to the skin surface at a desired site or sites. The formulation may be a solution, suspension, emulsion, cream, lotion, gel, foam, salve, ointment, powder, paste, vapor, tincture, solid (e.g., akin to a deodorant stick) etc. It rapidly, simply, and effectively reduced or eliminated unwanted fat and lipodystrophies for improved cosmetic appearance.

One embodiment of the invention is a transdermal formulation. One embodiment of the invention is a percutaneous formulation. In either or both of these embodiments, the composition may be applied to a surface and placed on the desired site(s) for transdermal and/or percutaneous delivery. The surface may be a tape, sponge, patch, etc.

The method induces adipose cell lysis in particular body areas of concern, i.e., areas having unwanted adipose cell aggregates. One embodiment of the method provides the composition in a structured lipid carrier for targeting adipose tissue that was previously accessible only by Injection. This nanostructure lipid carrier (NLC) technology is referred to as MIXED MICELLES LIPID NANOPEARLS™.

One embodiment is a topical formulation for reducing localized fat deposits in a mammal at one or more of these areas: under the eye, chin, around or on the face or arm, the buttock, calf, back, thigh, ankle, or stomach. One embodiment is a formulation for reducing specific types of fat deposits such as, e.g., eyelid fat herniation, lipomas, lipodystrophy, buffalo hump lipodystrophy, or fat deposits associated with cellulite. A composition with an effective amount of a pharmacologically active detergent and phosphatidylcholine mixtures with other excipients is topically applied. One embodiment locally administers a unit dose, repeated at least twice. The composition may contain a variety of pharmacologically active detergents as described. One embodiment uses a bile salt as the active detergent in the unit dose, preferably sodium deoxycholate. The methods may include administration of at least a second therapeutic agent as subsequently described. One embodiment uses an analgesic, preferably lidocaine, as the second therapeutic agent.

One embodiment is a topical dermatological preparation with scientifically proven capability of delivering both (a) into the subcutaneous tissue directly into or proximate the fat deposits using a nanostructured lipid carrier (NLC) (MIXED MICELLES-LIPID NANOPEARLS™) and (b) a specific chemical compound with documented clinical efficacy for dissolving fat deposits when introduced topically, subcutaneously, and/or percutaneously into and/or proximate fat deposits. In one embodiment, (b) is deoxycholic acid or its salts or derivatives. In one embodiment, (b) is a chemical with detergent effects, e.g., sodium lauryl sulfate. In these embodiments, the nanostructured lipid carrier delivers the active lipo-dissolving compound directly into and/or proximate the fat deposits. In either embodiment, the nanostructured lipid carrier may be associated with phosphatidylcholine and/or L-carnitine to facilitate fat metabolism.

Figure 1:
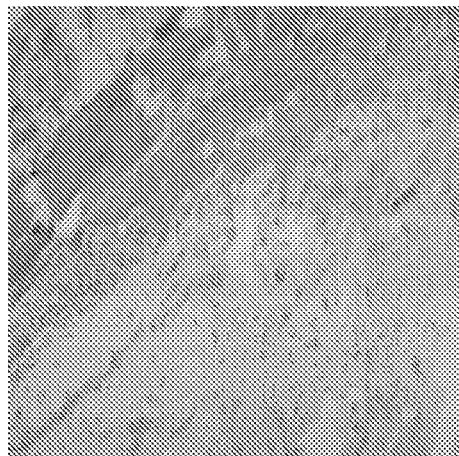
FIG. 1 shows histological sections of adipose tissue before (A) and after (B) topical administration of an embodiment of the inventive composition (PCDC), as well as skin penetration data (C) of the composition in a nanostructure lipid carrier (NLC).
Figure 1:
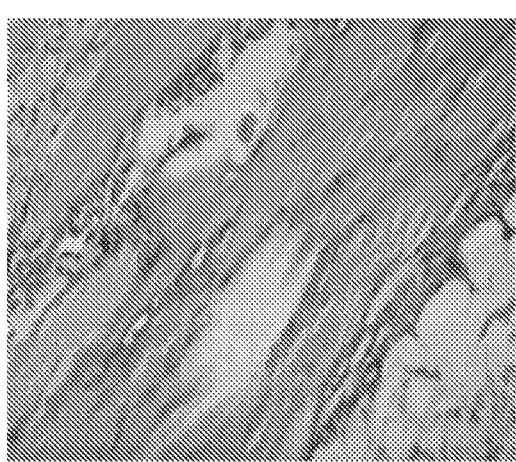
Figure 1:
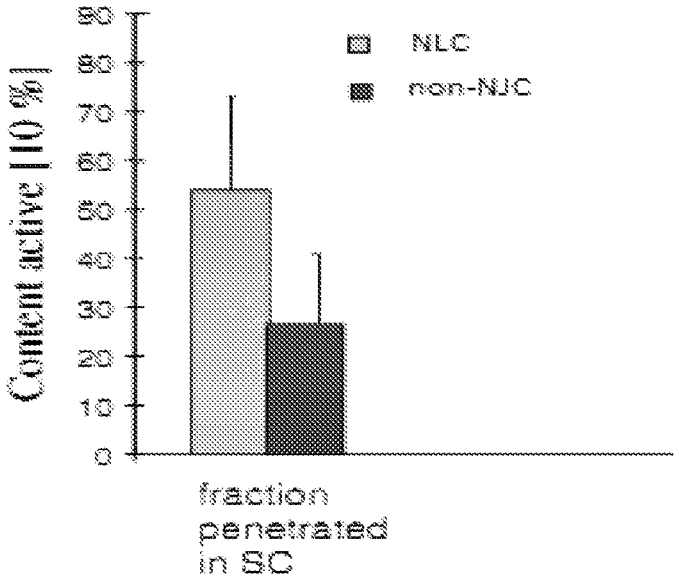

The inventive method and composition addressed the problem of localized fat accumulation in mammals without surgery or prolonged recovery time, with demonstrated clinical efficacy, and with fewer adverse side effects than previous methods. The method and composition non-surgically reduced fat deposits by topically administering fat-solubilizing concentrations of one or more detergents, e.g., bile salts, either alone or in combination with other lipo-dissolving detergents, in pharmaceutically acceptable formulations and dose formulations. The inventive compositions were non-invasively administered locally at a target site or sites.

One embodiment included one or more biologically compatible pharmacologically active detergents such as bile salts in an effective amount or concentration to dissolve fat, and pharmaceutically acceptable excipients, in an aqueous vehicle.

Examples of such biologically compatible pharmacologically active detergents include, but are not limited to, lipophilic detergents (whether ionic or non-ionic), hydrophilic detergents (whether ionic or non-ionic), ionic detergents, non-ionic detergents, zwitterionic detergents, glycerides, and bile salts.

Lipophitic detergents include, but are not limited to, alcohols, polyoxyethylene alkylethers, fatty acids, bile acids, glycerol fatty acid esters, acetylated glycerol fatty acid esters, lower alcohol fatty acids esters, polyethylene glycol fatty acid esters, polyethylene glycol glycerol fatty acid esters, polypropylene glycol fatty acid esters, polyoxyethylene glycerides, lactic acid derivatives of monddiglyc-erides, propylene glycol diglycerides, sorbitan fatty acid esters, polyoxyethylene sorbitan fatty acid esters, polyoxyethylene-polyoxypropylene block copolymers, transesteri-fied vegetable oils, sterols, sterol derivatives, sugar esters, sugar ethers, sucroglycerides, polyoxyethylene vegetable oils, polyoxyethylene hydrogenated vegetable oils, reaction mixtures of polyols and at least one member of the group consisting of fatty acids, glycerides, vegetable oils, hydrogenated vegetable oils, sterols, and mixtures thereof.

Non-ionic lipophilic detergents include, but are not limited to, alkylglucosides, alkylmaltosides, alkylthiogluco-sides, lauryl macrogolglycerides, polyoxyethylene alkyl ethers, polyoxyethylene alkylphenols, polyethylene glycol fatty acids esters, polyethylene glycol glycerol fatty acid esters, polyoxyethylene sorbitan fatty acid esters, polyoxy-ethylene-polyoxypropylene block copolymers, polyglycerol fatty acid esters; polyoxyethylene glycerides, polyoxyethyl-ene sterols, derivatives, and analogues thereof, polyoxyeth-ylene vegetable oils; polyoxyethylene hydrogenated veg-etable oils, reaction mixtures of polyols and at least one member of the group consisting of fatty acids, glycerides, vegetable oils, hydrogenated vegetable oils, and sterols, tocopherol polyethylene glycol succinates, sugar esters, sugar ethers, sucroglycerides, and mixtures thereof.

Ionic hydrophilic detergents include, but are not limited to, alkyl ammonium salts, bile acids and salts, analogues, and derivatives thereof; fatty acid derivatives of amino acids, carnitines, oligopeptides, and polypeptides; glyceride derivatives of amino acids, oligopeptides, and polypeptides; acyl lactylates; mono-, diacetylated tartaric acid esters of mono-, diglycerides; succinoylated monoglycerides; citric acid esters of mono-, diglycerides; alginate salts; propylene glycol alginate; lecithins and hydrogenated lecithins; lyso-lecithin and hydrogenated lysolecithins; lysophospholipids and derivatives thereof, phospholipids and derivatives thereof; salts of alkylsulphates; salts of fatty acids; sodium docusate; and mixtures thereof.

Examples of ionic detergents include, but are not limited to, cholate, sodium deoxycholate, sodium dodecylsulfate and C-16 TAB. In one embodiment, sodium deoxycholate is used as an ionic detergent.

Non-ionic detergents include, but are not limited to, Brij 35, n-alkyl PEO monoether such as, polyoxylethylen(20) cetyl ether, Lubrol PX, Lubrol wx, nonidet P-40, n-alkyl phenyl PEO such as, octylphenolpoly(ethyleneglycolether) n10, and octylphenolpoly(ethyleneglycolether)n7, tetram-ethylbutylphenyl PEO, n-octylglucoside, octyl-thioglucopy-ranoside, tween-80 and tween-20, and alkylaryl polyether alcohol (Triton®X-100).

Zwitterionic detergents include, but are not limited to, 3-[(3-cholamidopropyl)d imthylammoniojpropane-sulfonate (CHAPS), N-tetradecyl-N,N-dimethyl-3-ammo-niu-1-propanesulfonate, cholic acid sulfobetaine, lauryidi-methylbetaine (Empigen® BB) and zwittergent 3-14.

Glycerides include, but are not limited to, mono-, di- or tri-glycerides. Triglycerides include, but are not limited to, vegetable oils, fish oils, animal fats, hydrogenated vegetable oils, partially hydrogenated vegetable oils, synthetic triglyc-erides, modified triglycerides, fractionated triglycerides, and mixtures thereof.

Bile salts include, but are not limited to, steroids having 1-3 hydroxyl groups and a five carbon atom side chain terminating in a carboxyl group, which can be conjugated to glycine or taurine. Additional examples of bile salts include salts of cholate, deoxycholic, cholic, chenodeoxycholic, 7-alpha-dehydroxylate, chenodeoxycholic, lithocholic, ursodeoxycholic, dihydroxy- and trihydroxy- and taurine or glycine conjugates of any of the above. In one embodiment, the bile salt is sodium deoxycholate.

One embodiment is a method of treating, i.e., providing clinically demonstrable results, of lipid-related conditions in a patient, such as lipomas, using a detergent or combination of detergents that are topically applied to or proximate the affected area. Detergents used in the method include, but are not limited to, anionic detergents, cationic detergents, zwit-terionic detergents, ampholytic detergents, amphoteric detergents, nonionic detergents, particularly nonionic deter-gents having a steroid skeleton. Mixtures of such detergents can also be used. The detergent can be synthetic, natural, or semi-synthetic. In one embodiment, anionic detergents are used.

Cationic detergents include, but are not limited to, hexa-decyl(cetyl)trimethyl-ammonium, dodecylpyridinium chlo-ride, dodecylamine hydrochloride, cetyl-trimethyl-ammo-nium-bromide (e.g., Cetrimide B.P.), and benzalkonium chloride.

Zwitterionic detergents include, but are not limited to, Zwittergent 3-08(n-octyl-N,N-dimethyl-3-ammonio-1-pro-panesulfonate), Zwittergent 3-10(n-decyl-N,N-dimethyl-3-ammonio-1-propanesulfonate), Zwittergent 3-12(n-dodecyl-N,N-dimethyl-3-ammonio-1-propanesulfonate) (Calbiochem, LaJolla CA), and betaine and betaine-like detergents where the molecule contains both basic and acidic groups that form an inner salt giving the molecule both cationic and anionic hydrophilic groups.

Ampholytic and amphoteric detergents can be either cationic or anionic depending on the pH of the solution. An example of an ampholytic detergent that may be suitable is the ear wax solution is N-dodecyl-N,N-dimethyl betaine. An example of an amphoteric detergent that may be suitable is alkyl dimethylamine betaine (e.g., Empigen B B (Albright & Wilson, Richmond VA). Other nonlimiting examples of amphoteric and ampholytic detergents that may be suitable are dodecylbeta-alanine, N-alkyltaurines, N-higher alkylaspartic acids, and the detergents.

In a preferred embodiment, the detergent is selected from the category of detergents having a steroid skeleton. Anionic detergents having a steroid skeleton may include, but are not limited to, sodium deoxycholate, sodium cholate, sodium taurocholate, and sodium taurodeoxycholate. Nonionic detergents having a steroid skeleton may include, but are not limited to, N,N-Bis(3-D-gluconamidopropyl)cholamide, N,N-Bis(3-D-gluconamidopropyl)-deoxycholamide, and digitonin. Zwitterionic detergents having a steroid skeleton may include, but are not limited to, 31(3-cholamidopropyl) dimethylammonio]-propanesulfonic acid (e.g., CHAPS). Other categories of detergents having a steroid skeleton may also be suitable.

In a preferred embodiment, the detergent having a steroid skeleton is a natural, semi-synthetic, or synthetic bile salt. Naturally occurring bile salts are biological detergents synthesized in the liver. The commonly occurring bile acids include cholic acid, deoxycholic acid, lithocholic acid, chenodeoxycholic acid, hyodeoxycholic acid, and hyocholic acid. The bile acid can be a primary or secondary bile acid. The bile salts include alkali metal salts of such acids, such as sodium deoxycholate and sodium cholate.

Pharmaceutical agents include insulin, heparin, low molecular weight heparin, hirulog, hirugen, huridine, cytokines, mono and polyclonal antibodies, immunoglobins, high molecular weight proteins and peptides, chemotherapeutic agents, vaccines, glycoproteins, bacterial toxoids and bacterial and non-bacterial toxins, calcitonins, glucagon like peptides, thrombolytic compounds, platelet inhibitors, DNA, RNA, gene therapeutics, antisense oligonucleotides, vasodilators, antihypertensives, anti diabetes drugs and therapies, anti acids, moisturizers, wound healing compounds, pain killers, antibiotic agents, antimicrobial agents, anti-acne agents, antibacterial agents, antifungal agents, antiviral agents, steroidal anti-inflammatory agents, non-steroidal anti-inflammatory agents, anesthetic agents (various caines and non-caines), antipruriginous agents, antiprotozoal agents, anti-oxidants, antihistamines, vitamins, and hormones.

Hormones that may be included in the inventive compositions include, but are not limited, to thyroids, androgens, estrogens, prostaglandins, somatotropins, gonadotropins, erythropoetin, interferons, steroids and cytokines. Cytokines are small proteins with the properties of locally acting hormones and as used herein include, but are not limited to, various forms of interleukin (IL), and growth factors including various forms of transforming growth factor (TGP), fibroblast growth factor (FGF) and insulin-like growth factor (IGF). Vaccines that may be used in the inventive composition include bacterial and viral vaccines such as vaccines for hepatitis, influenza, tuberculosis, canary pox, chicken pox, measles, mumps, rubella, pneumonia, BCG, HIV and AIDS; bacterial toxoids or toxins include but are not limited to diphtheria, tetanus, botullinum, *Pseudomonas* sp. and *Mycobacterium tuberculosis*. Examples of drugs, more specifically cardiovascular or thrombolytic agents, include heparin, hirugen, hirulos and hirudine. Macromolecular pharmaceutical agents included in the invention include monoclonal antibodies, polyclonal antibodies and immunoglobins.

None of the previous lists are inclusive or exhaustive; all are exemplary only and not limiting.

The macromolecular pharmaceutical agent exists in micellar form in the inventive pharmaceutical compositions. Micelles likely significantly aid in the absorption of the macromolecular pharmaceutical agent, both because of their enhanced absorption ability, and also because of their size. In addition, encapsulating pharmaceutical agents in micelles protects the agents from rapid degradation in the environment of the gastrointestinal tract.

In a preferred embodiment, the composition includes a plurality of detergents. For example, the composition may contain sodium deoxycholate and sodium dodecyl sulphate. The detergent can be used in any suitable amount or concentration in the composition. In one embodiment, the composition includes from about 0.5% by weight to about 30% by weight of the detergent. In one embodiment, the composition includes from about 1% by weight to about 15% by weight of the detergent.

In embodiments, the composition includes a solvent for the detergent. In embodiments, the solvent is water, a hydrophilic solvent, or a mixture thereof. Examples of hydrophilic solvents include, but are not limited to, alkylalcohols such as isopropanol, methanol, ethanol, n-propanol, n-butanol, secondary butanol, tertbutanol and isobutanol, alkylene glycols such as propylene glycol and polyethylene glycol, ether alcohols such as methyl cellosolve, ethyl cellosolve, propyl cellosolve, butyl cellosolve, methyl carbitol and ethyl carbitol, ether esters such as methyl cellosolve acetate and ethyl cellosolve acetate, dioxane, dimethylformamide, diacetone alcohol, methyl ethyl ketone, acetone, tetrahydro-furfuryl alcohol, and mixtures thereof.

In embodiments, the composition includes an alkaline material. Examples of alkaline materials include the sodium, potassium, calcium, magnesium and aluminum salts of phosphoric acid, carbonic acid, citric acid, and certain aluminum/magnesium compounds. Other examples include antacid materials such as aluminum hydroxides, calcium hydroxides, magnesium hydroxides and magnesium oxide. A preferred alkaline material used in the composition is disodium phosphate. Any suitable amount of alkaline material can be used in the composition. Generally, the amount or concentration of alkaline material in the composition is between about 0.1% by weight and about 5% by weight of the composition.

In some embodiments, the product also includes an ionic additive effective to increase the ionic strength of the composition. For example, the ionic additive may be an alkali metal salt, such as an alkali metal salt of a halogen. Examples of suitable ionic additives include, but are not limited to, sodium chloride, potassium chloride, sodium bromide, potassium bromide, sodium iodide, potassium iodide and the like. Any suitable amount or concentration of ionic additive can be used in the composition. Generally, the amount or concentration of ionic additive in the composition is between about 0.1% by weight and about 5% by weight of the product.

The composition is formulated to have a suitable pH. In embodiments, the composition pH ranges between about pH 5 to about pH 11.5. The particle size of the micelles typically range from 1 nanometer (nm) to 10 nm to 100 nm. Preferably, the micelle size ranges between 1 nm and 5 nm.

The composition is useful and is used in clinical situations including, but not limited to, dissolving lipomas, fat, mesotherapy, separating tissue, tumor reduction, cancer reduction, cancer treatment, and other clinical situations where it is desirable to loosen, remove, assist the body consumption or resolution of wax, lipids, proteins, or carbohydrates from a part or region of the body. For example, the inventive composition is administered subcutaneously in contact with a lipomas to dissolve the lipoma, either alone or with other more invasive administration methods such as subcutaneous injection.

The composition may be useful in ameliorating conditions such as granulomas, scars, tumors, acne cysts, sebaceous cysts, sebaceous hyperplasia, diseases of the sebum, acne related dermatoses, diseases of the subcutaneous fat, tumors, tattoo removal, infections and biofilms, cellulite, fatty deposits, fat tissue, and related conditions. The composition may be useful to even out skin contour defects, such as breast or lip asymmetry after over-correction with a skin filler, or a hyperresponse of the body to an injection. It can also be used as a cosmetic anti-wrinkle treatment using various compounds such as hyaluronic acid (HA), toxins, collagen, elastins, vitamins C, B, A, E, etc.

In the embodiment including micelles, the inventive compositions further comprise at least one micelle-forming compound. The micelle-forming compound may be lecithin, octylphenoxypolyethoxy-ethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, hyaluronate and its derivatives, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof. In one embodiment, the micelle-forming compound is present in the composition in a concentration between about 1 wt./wt.°/0 and 20 wt./wt. % of the total composition. In one embodiment, the micelle-forming compound is present in the composition in a concentration of between about 1 wt./wt. % and 5 wt./wt. % of the total composition. The alkali metal alkyl sulfate functions as a micelle forming agent, and is added to the composition in addition to the one or more other micelle-forming compounds. The total concentration of alkali metal alkyl sulfate, the alkali metal salicylate, the edetate, and the micelle-forming compounds together is less than 50 wt./wt. % of the total composition.

The lecithin can be saturated or unsaturated, and is preferably selected from the group consisting of phosphatidylcholine, phosphatidylserine, sphingomyelin, phosphatidylethanolamine, cephalin, and lysolecithin and mixtures thereof. Saturated and unsaturated lecithin are commercially available from The American Lecithin Co. as Phospholipon-H and Phospholipon-G, respectively.

In one embodiment, at least two micelle-forming compounds are used. The micelle-forming compound combination is selected from the group consisting of saturated and unsaturated phospholipid; lecithin and lactic acid and glycolic acid; lactic acid, linoleic acid and evening of primrose oil; saturated phospholipid and glycolic acid, and hyaluronic acid; saturated phospholipid, glycolic acid and lactic acid; sodium hyaluronate, oleic acid, and gamma linoleic acid; and trihydroxy oxocholanyl glycine, lecithin, and chenodeoxycholate.

The above-described components of the inventive composition are in a suitable solvent. Water is a preferred solvent but other suitable solvents include alcohol solutions, especially ethanol. Alcohol should be used at concentrations that will avoid precipitation of composition components. Sufficient solvent should be added so that the total of all components in the composition is 100 wt/wt %, i e. solvent to quantity sufficient (q.s.). Typically, some portion of the solvent will be used initially to solubolize the pharmaceutical agent prior to adding the micelle-forming compounds.

The composition will typically contain between about 1 wt./wt. % to 20 wt./wt. % of the solvent, depending on the desired dilution and dosage.

The inventive compositions optionally contain a stabilizer and/or a preservative. Phenolic compounds are particularly suited for this purpose as they both stabilize the composition and protect against bacterial growth. A phenolic compound has one or more hydroxy groups attached directly to a benzene ring. Preferred phenolic compounds used in the inventive composition include phenol, methyl phenol (also known as m-cresol), and combinations thereof.

The composition may contain fragrance and/or flavor agents, e.g., menthol, sorbitol, fruit, etc. Menthol may be used as an absorption enhancing compound, and also acts as a cooling and soothing agent.

The antioxidant can be selected from the group consisting of tocopherol, deteroxime mesylate, methyl paraben, ethyl paraben, ascorbic acid and mixtures thereof, as well as other antioxidants known in the pharmaceutical arts. A preferred antioxidant is tocopherol. Parabens also provide preservation to the composition.

Protease inhibitors inhibit degradation of the pharmaceutical agent by the action of proteolytic enzymes. When used, protease inhibitors are preferably in a concentration of between about 1 and 3 wt./wt. % of the composition. Any material that can inhibit proteolytic activity can be used, absent compatibility problems. Examples include, but are not limited, to bacitracin and bacitracin derivatives such as bacitracin methylene disalicylates, soybean trypsin, and aprotinin. Bacitracin and its derivatives are preferably in a concentration of between 1.5 wt./wt./% and 2 wt./wt. % of the total composition. Soybean trypsin and aprotinin are preferably in a concentration of between about 1 wt. %/wt. % and 2 wt./wt. % of the total composition.

An isotonic agent such as glycerin or dibasic phosphate may also be added after formation of the mixed micelle composition. The isotonic agent maintains micelles in solution. When glycerin is used as one of the micelle-forming compounds it will also function as an isotonic agent. When dibasic sodium phosphate is used as one of the micelle-forming compounds it will also inhibit bacterial growth.

The composition pH should typically be in the range of pH 5 to pH 8, more preferably in the range of pH 6 to pH 7. Hydrochloric acid or sodium hydroxide can be utilized to adjust the composition pH as needed.

The inventive composition may be stored at ambient or room temperature, i.e., about 19° C. to about 22° C., or at cold temperature, i.e., about 4° C. Storage of proteinic drugs is preferable at a cold temperature to prevent drug degradation and to extend their shelf life.

The invention provides a pharmaceutical composition in which a macromolecular pharmaceutical agent is encapsulated in mixed micelles formed by a combination of micelle-forming agents. Topical application provides easy access to membrane sites, so that the drug can be applied, localized, and removed easily. Prolonged delivery of large molecules may be achieved through these membranes. While topical administration is preferable and provided clinically proven therapy, in one embodiment the composition may be administered by injection.

In one embodiment, a mixed micelle composition is prepared. At least one micelle-forming compound, a pharmaceutically active agent, and at least an alkali metal alkyl sulfate, edetate, and an alkali metal salicylate, and is mixed under conditions to result in a first micelle composition. The first micelle composition is then mixed with at least one additional micelle-forming compound to form a mixed micelle composition. In one embodiment, additional micelle-forming compounds are added, either the same or different from those in the first micelle-forming compound. In one embodiment, the first micelle-forming compound is lecithin.

Any optional agent may be added to the composition during or after adding the additional micelle-forming compound. As one example, a stabilizer, preferably phenol and/or m-cresol, may be added during or after adding the additional micelle-forming compound to the mixed micelle composition to stabilize the formulation and protect against bacterial growth. As one example, an isotonic agent may be added during or after adding the additional micelle-forming composition. The formulation can then be put into an aerosol dispenser and the dispenser charged with propellant, if administration by this route is desired. The dispensed dose of pharmaceutical agent is propelled from the metered valve in a fine spray.

In one embodiment, the formulation comprises about 5% (w/w) phospholipids, e.g. in the form of lecithin, about 10% w/w deoxycholic acid or a salt thereof, and a mix of micelle-forming compounds including glycolic acid (1%) and sodium lauryl sulfate and DMSO (1.0%-0.5%), components to enhance both lipolysis and fatty acid oxidation including Azelaic-Kojic Acid mixture (3%) and hyaluronidase-collagenase-artichoke mixture (3%), a diuretic to stimulate lymphatic drainage and direct lipolysis including an L-carnitine-aminophylline mixture (3%), thiamine (Vitamin B1) (1%), riboflavin (B2) (1%), niacin (B3) (1%), pantothenic acid (B5) (1%), pyridoxine (B6) (1%), and caffeine (1%) to enhance metabolic reactions and stabilize the formulation.

In another embodiment, the formulation comprises about 0.5% w/w phospholipids (e.g. 0.01-0.5%) and less than 10% w/w deoxycholic acid or a salt thereof, e.g. 5-10%, such as 9.0% deoxycholic acid or a salt thereof such as sodium deoxycholate. The formulation may additionally include excipients such as micelle-forming compounds as herein described, for example, sodium lauryl sulfate, polyoxyethylene lauryl ether, 2-hydroxyethyl octadecanoate, olive oil, stearic acid, evening primrose oil, and the like.

In another embodiment, the formulation may additionally include agents which function to supplement lipolysis, including agents which function to solubilize fat, reduce cellulite, prevent accumulation of fat and the like. Exemplary agents include, but are not limited to, bitter orange extract, glycyrrhetinic acid, *Ginkgo biloba*, aloe barbadensis leaf extract, L-carnitine, *Nelumbo nucifera* leaf extract, as would be known to those of skill in the art. Such agents are particularly useful in formulations in which the bile acid content is less than 10% w/w, and advantageously result in a formulation which unexpectedly substantially retains efficacy with substantially reduced undesirable side effects such as redness, burning and itch.

The process to formulate the nanostructured lipid carriers is as follows:

(a) mixing under high velocity high shear conditions a macromolecular pharmaceutical agent in a suitable solvent, an alkali metal alkyl sulfate, an edetate, and an alkali metal salicylate. In an ultra-high-shear inline mixer, the high-shear mixing occurs in a single pass or in multiple passes through a rotor-stator array. The mixing conditions subject the composition to higher shear and a larger number of shearing events than a standard inline rotor—stator mixer, producing exceptionally narrow particle-size distribution with sub-micrometer particle sizes possible.

(b) subsequently adding at least one micelle-forming compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof, to form a first micelle macromolecular pharmaceutical agent composition; and (c) after step (b), adding at least one additional micelle-forming compound different from that added in step (b) but selected from the same group. Preferably, the micelle-forming compound in step (b) is lecithin.

During or after step (b), a phenolic compound as described above can be added to the composition. Mixing can be vigorous or not. Vigorous mixing may be by high-speed stirrers, such as magnetic stirrers, propeller stirrers, or sonicators, and is preferred.

The invention also provides a metered dose aerosol dispenser with the inventive composition and a propellant contained therein, in which a solution containing the macromolecular pharmaceutical agent and the propellant are in a single phase. The formulation can be administered by a metered dose pump container for oral, nasal, ear, rectal, vaginal, or submucosal delivery using variety of drugs, hormones, peptides, etc.

The following non-limiting examples further disclose the invention.

EXAMPLE 1

A formulation was prepared using 5% (w/w) phospholipids (Phospholipon-G, American Lecithin), of which 98% are phosphatidylcholine; i.e., this preparation contained 46.5 mg (5% w/w) of phosphatidylcholine and 46.6 mg deoxycholic acid. In a mixture (50/50) ethyl alcohol/isopropyl alcohol) with (10%) deoxycholic acid or salts of deoxycholic acid, glycolic acid (1%), sodium lauryl sulfate and DMSO (1.0%-0.5%), Azelaic-Kojic Acid mixture (50/50) (3%), hyaluronidase-collagenase-artichoke mixture (50/50) (3%) to enhance both lipolysis and fatty acid oxidation, L-Carnitine-Aminophylline mixture (50/50) (3%), a diuretic to stimulate lymphatic drainage and direct lipolytic, thiamine (Vitamin 131) (1%), riboflavin (B2) (1%), niacin (B3) (1%), pantothenic acid (B5) (1%), pyridoxine (B6) (1%), and caffeine (1%) to enhance metabolic reactions and stabilize the formulation by preventing phosphatidylcholine oxidation.

Therapy using the above formulation acts in two different ways: by a lipolytic effect on adipose cell deposits, and by a venotonic and drainage effect on the circulatory system. The formulation uses the skin's water/alcohol based "channels" to permit drug penetration into the skin by controlled "electroporation-like" electrical pulses, the same as or similar to mesotherapy with no needles required.

Phospholipon H or G was dissolved in a mixture of ethyl alcohol and isopropyl alcohol with gentle stirring and heating to 40° C. This solution was then kept warm to prevent solidification. In a separate beaker 5% wt./wt. phospholipids (Phospholipon-G, American Lecithin), e.g. phosphatidylcholine (5%) and deoxycholic acid (10%) were dissolved in water at 50° C. with vigorous stirring. To this solution sodium lauryl sulfate and DMSO (0.5%), Azelaic-Kojic Acid mixture (50/50) (3%), hyaluronidase-collagenase-artichoke mixture (3%), (L)-carnitine-aminophylline mixture (50/50) (3%), thiamine (Vitamin B1) (1%), riboflavin (132) (1%), niacin (B3) (1%), pantothenic acid (B5) (1%), pyridoxine (B6) (1%), and caffeine (1%) by weight were added and the solution was vigorously stirred at ultra high speed, 2000 rpm or higher at 50° C. The solution pH was adjusted to about pH 5. This solution was then added slowly, e.g., dropwise, to a white cream base to result in a white cream/emulsion with continuous high speed stirring. The cream base was cooled to room temperature (about 20° C.) and was stored in a glass beaker away from direct heat and sunlight.

EXAMPLE 1.2

A formulation having the following components was made by mixing the following phases in order.

| % | PHASE A - Component | Function |
|---|---|---|
| 29.38% | Water | solvent-diluent |
| 0.750% | sodium lauryl sulfate | emulsifier-detergent |
| 3.0% | Azelaic-Kojic Acid mixture (50/50) | preservative antimicrobial |
| 3.0% | hyaluronidase-collagenase-artichoke mixture | skin-conditioning agent |
| 3.0% | (L)-carnitine-aminophylline (50/50) | emollient, preservative, solvent |
| 5.000% | isopropyl alcohol | antiseptic, antimicrobial, solvent |

| % | PHASE B - Component | Function |
|---|---|---|
| 14.100% | stearic acid | binder, viscosity increasing agent, emulsifier agent |
| 2.820% | glyceryl stearate | emollient, skin conditioning agent |
| 3.0% | niacin | emollient, solvent, skin conditioner |
| 1.000% | olive oil | viscosity increasing agent, emulsifier agent, solvent |
| 4.00% | dimethicone | skin protectant, conditioner, emollient |
| 3.500% | MYRJ 52 (2-hydroxyethyl octadecanoate) | surfactants - non-ionic-detergent, emollient |
| 4.000% | ethyl alcohol (pure) | antiseptic, antimicrobial, solvent |
| 2.0% | caffeine | emulsifier agent, solvent |
| | PHASE C | |
| 5.000% | linoleic acid | anti-irritants, emollient skin smoothing agent |
| 0.500% | tocopherol acetate | Promotes healing, anti-inflammatory, antioxidant, humectant, exfolient |
| 5.700% | lactic acid 88% | |
| 5.00% | niacinamide | (Vitamin B3), anti-redness, moisturizer, anti-inflammatory, oil control, skin lightening |
| 0.800% | evening primrose oil | treat dry, scaly, or itchy skin conditions, improves skin texture |
| | PHASE D | |
| 2.000% | lecithin - (phospholipon g) | delivery system, emulsifier, skin-conditioning, surfactant |
| 20.000% | sodium deoxycholate | delivery system, emulsifier, skin-conditioning, surfactant |
| 0.750% | BRIJ 35 (polyoxyethylene lauryl ether) | emulsifier |
| | PHASE E | |
| 0.500% | phenoxyethanol | anti-microbial |
| 0.500% | caprylyl phenoxyethanol | anti-microbial |
| | PHASE F | |
| 0.500% | TEA (triethanolamine) | Cleanser, anti-microbial agent |

EXAMPLE 1.3

The solution of Example 1.2 was then added slowly, e.g., dropwise, to a white cream base to result in a white cream/emulsion with continuous high speed stirring. The cream base was cooled to room temperature (about 20° C.) and was stored in a glass beaker away from direct heat and sunlight.

EXAMPLE 2

Animal Clinical Study

The local reaction of one embodiment of the inventive composition was determined on mouse abdominal subcutaneous adipose tissue in vivo.

Mice were treated topically (abdominal skin) with phosphatidylcholine (PC) and deoxycholate (DC), termed PCDC (10% DC, 5% PC) formulated as a cream and administered in an amount of 0.2 mL per dose. Mice were also treated topically with a corresponding volumes of a control dose (containing no PCDC). Control and treatment administrations occurred for 30 days (n=15 mice per dose). Mice were euthanized on day 30, and biopsy specimens were obtained from the treated sites (n=3 per dose). The entire abdominal skin with adherent subcutaneous fat was peeled off using tweezers and sharp scissors. The flap was placed in a petri dish inside out and three biopsy tissues were fixed in formaldehyde, paraffin-embedded, and stained with hematoxylin and eosin. Four micrometer sections were evaluated to judge the outcome and to determine treatment efficacy.

Calcein fluorescence was measure in biopsy tissues to determine whether topically applied PCDC resulted in disruption of cell membranes. The treatment destroyed almost all cells as expected. These data demonstrated that cell lysis was associated with cell death in PCDC treated adipose tissue and manifested about four weeks after dosing, but could also have begun earlier.

FIGS. 1A and 1B show light microscopy of histologic sections of rat subcutaneous adipose tissue biopsies before (FIG. 1A) and after 30 days (FIG. 1B) of PCDC topical administration. Cell lysis increased by 45% and 55%, respectively ($p<0.05$) vs. untreated control tissue. The data demonstrated that repeated administration of PCDC over the course of one month significantly enhanced cell membrane and mitochondrial dysfunction and cell viability. FIG. 10 shows skin penetration data of the composition in a nano-structure lipid carrier (NLC) formulation (as described in Example 1) compared to a composition not in a NLC formulation (PCDC).

EXAMPLE 3

Human Clinical Study

The effects of PCDC treatment on tissue and histologic changes were evaluated.

After obtaining informed consent, patients who sought treatment for fat deposits were treated with PCDC. Twenty patients (17 female, 3 male) were provided topical applications of PCDC formulations for treatment of localized fat. Patient ages ranged from 37 to 72 years for women, and from 32 to 47 years for men; mean age was 53.4 years.

The PCDC formulation contained 10% DC and 5% PC in a cream base. The initial concentration of PC was 100 mg/mL, and the initial concentration of DC was 50 mg/mL according to the monograph of the medicine registered with the United States Pharmacopoeia (USP). The cream 1 mL dose was applied to each of the treated areas twice a day for 30 days. Upon the application, the patient reported a mild burning or tingling sensation which was gone within 5-7 minutes. The technique used for facial and neck treatment was gentle massage after the application of 1 mL of the inventive PCDC cream formulation for deep subcutaneous penetration with ultrasonic or high frequency ultrasound device massage for 60 seconds.

Depending upon the needs of each patient, there were five or more clinical sessions, with intervals of one week. Needs were based on the initial medical evaluation and according to the results obtained from subsequent applications. Patients were requested to report any side effects that occurred during the treatment period. Digital photographs were taken before initiating treatment and at the end of the treatment course. A follow-up questionnaire was administered by telephone after the last treatment. Patient satisfaction with the treatment was evaluated as satisfied or unsatisfied. In those patients who responded that they were satisfied, the degree of reduction of localized fat was evaluated as discreet, moderate, or marked. Patients were also asked whether the reduction of localized fat was persistent after application.

Figure 2:
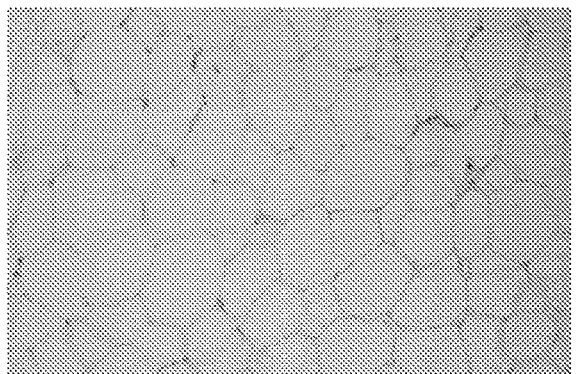
FIG. 2 shows subcutaneous adipose tissue biopsy results pre- and 6 weeks post-treatment by an embodiment of the inventive methods from control (A/C) and treated (B/D) patients.
Figure 2:
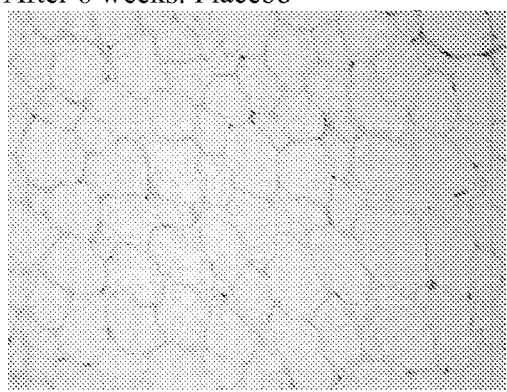
Figure 2:
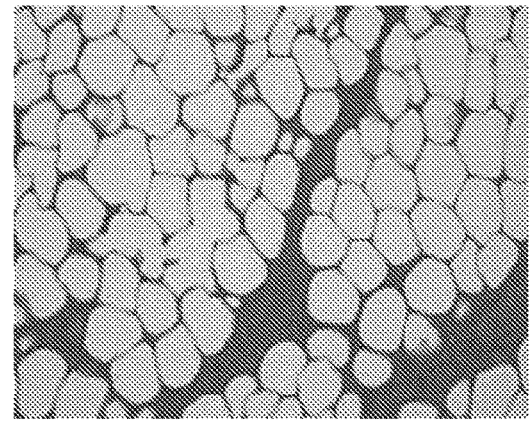
Figure 2:
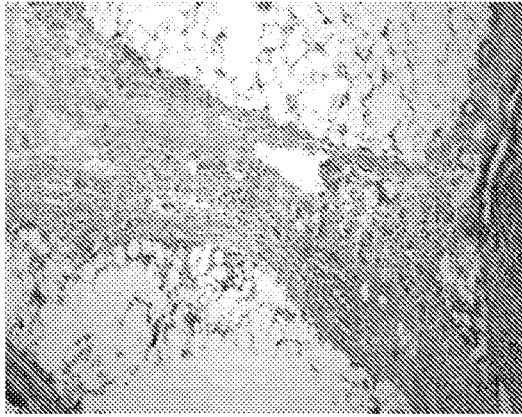
Figure 3:
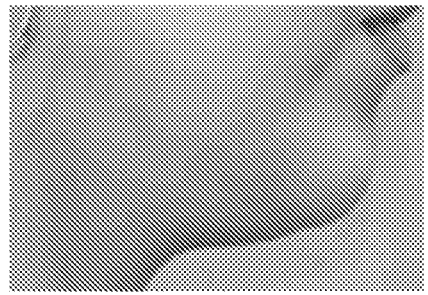
FIG. 3 shows photographs of subjects pre- (A, C, E, and G) and 60 days post-treatment (B, D, F, and H) by an embodiment of the inventive method.
Figure 3:
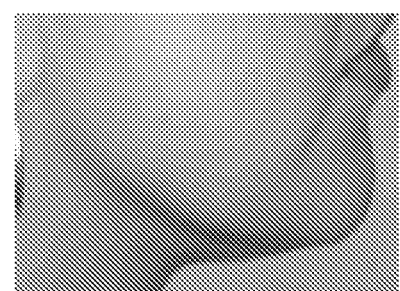
Figure 3:
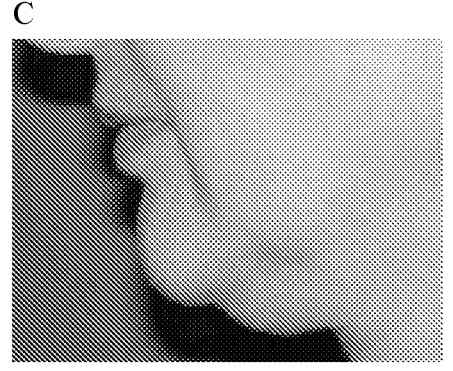
Figure 3:
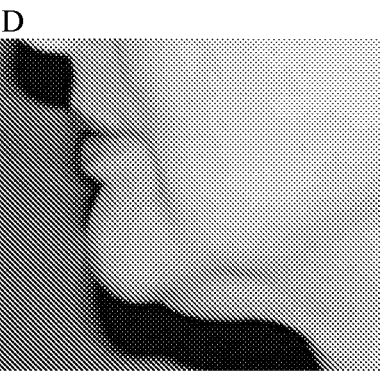
Figure 3:
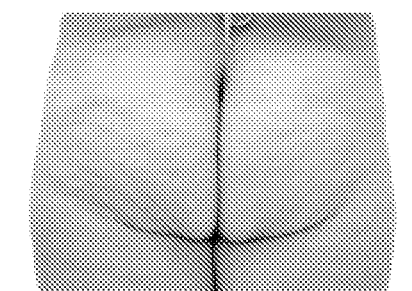
Figure 3:
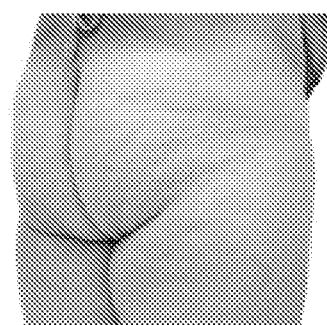
Figure 3:
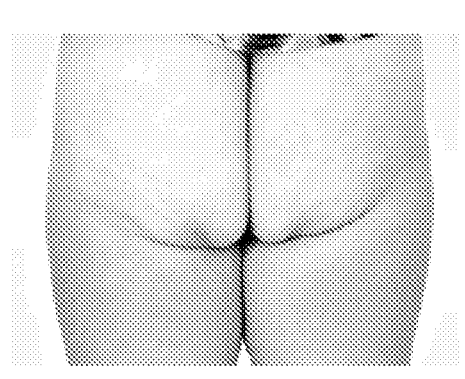
Figure 3:
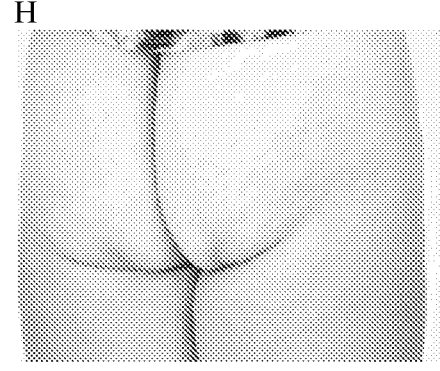
Figure 4:
FIG. 4 shows photographs of a subject pre- (A/B) and 60 days post-treatment (C/D) by an embodiment of the inventive method.
Figure 4:
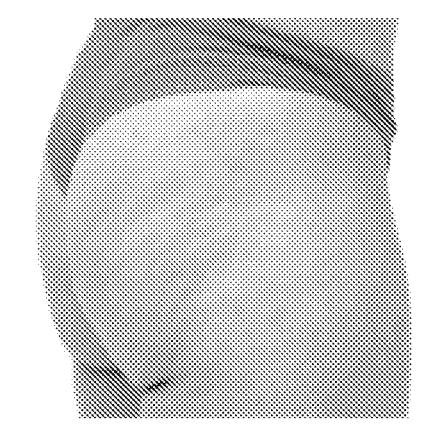
Figure 4:
Figure 4:
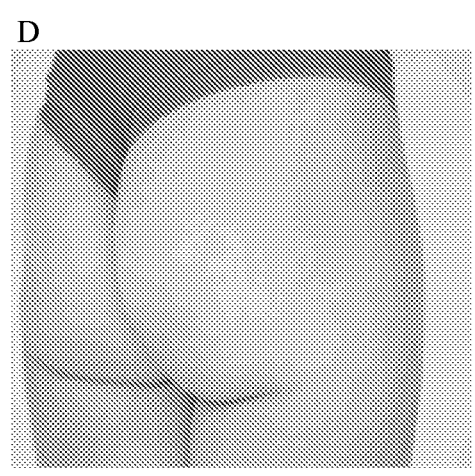

Four mm punch biopsies were obtained post-treatment. The biopsy tissue was placed in formalin and submitted for histological examination. Paraffin sections were obtained and the tissue was stained with hematoxylin and eosin. Results are shown in FIGS. 2A-D. FIG. 2A shows pre-treatment patient receiving placebo; FIG. 2B shows 6 weeks post-treatment patient receiving placebo. There was no change from baseline in patients receiving placebo. FIG. 2C shows pre-treatment patient receiving one embodiment of the inventive composition. FIG. 2D shows 6 weeks post-treatment patient receiving one embodiment of the inventive composition.

Results 60 days post-treatment of subject 1 are shown in FIGS. 3A-H. Photographs of pre- and post-treatment of chin (FIGS. 3A-D), and buttocks and upper thigh (FIGS. 3E-H) are shown. Results 60 days post-treatment of subject 2 are shown in FIGS. 4A-D, and results on ultrasound on both thighs of subject 2 are shown below:

| ULTRASOUND OF BOTH THIGHS | | | | | | |
|---|---|---|---|---|---|---|
| LEFT | | | | | | |
| | POSTERIOR | | | LATERAL | | |
| | SUP | MID | INF | SUP | MID | INF |
| Jun. 5, 2013 | 2.4 | 1.6 | 1.3 | 4.7 | 3.3 | 2 |
| Jul. 3, 2013 | 3.3 | 2 | 1.8 | 3.8 | 2.5 | 1.1 |
| Jul. 31, 2013 | 2.3 | 1.7 | 1.3 | 3.7 | 2.4 | 1.4 |
| Aug. 28, 2013 | 2.2 | 1.7 | 1.2 | 3.6 | 2.4 | 1.4 |
| Sep. 25, 2013 | 2 | 1.5 | 1.1 | 3.6 | 2.4 | 1.4 |
| RIGHT | | | | | | |
| | POSTERIOR | | | LATERAL | | |
| | SUP | MID | INF | SUP | MID | INF |
| Jun. 5, 2013 | 2.5 | 2 | 1.6 | 4.9 | 3.5 | 2.1 |
| Jul. 3, 2013 | 2.5 | 2 | 1.6 | 3.9 | 2.6 | 1.6 |
| Jul. 31, 2013 | 2.3 | 1.8 | 1.4 | 3.7 | 2.4 | 1.6 |
| Aug. 28, 2013 | 2.2 | 1.7 | 1.3 | 3.7 | 2.3 | 1.6 |
| Sep. 25, 2013 | 2.2 | 1.6 | 1.2 | 3.7 | 2.3 | 1.6 |

These data are the thickness of the tissue fatty mass from the outermost external skin surface to the end of the tissue fatty mass. Measurements were taken at three selected points for each patient consistently, as marked by the clinician before and during the trial.

Three of the 20 treated patients experienced side effects of mild itching or a tingling sensation on the first and second days after the treatment. These side effects disappeared in a short time. Of the sample of 20 patients, 18 (90%) reported reduction in the deposits of localized fat on the thigh and face after the PCDC treatment after eight weeks. Of the sample of 20 patients, 13 reported marked reduction in cellulites, 6 reported moderate reduction, and 1 reported mild reduction.

The demand for less-invasive techniques for fat reduction has provoked alternative treatments. The inventive method and composition yielded final results comparable to both liposuction and surge. Until this invention, the only treatment has been liposuction and/or surgery.

This inventive method and composition provided a simple, rapid procedure without surgical risks. The cosmetic results were satisfactory both from the patient and dermatologist points of view. Despite temporary side effects such as minor redness, itching, and slight tingling that caused a degree of discomfort, and without being limited to a specific theory, a postulated mechanism of action is based on fat cell destruction by the detergent action on cell membranes, with a true adipocitolysis, and a later emulsification of the released fatty acids by means of PPC. Deoxycholate alone appears capable of inducing fat cell destruction, i.e., lipoclasis and not lipolysis, in a specific fashion due to its detergent action, but its more important and slowly resolving side effects may indicate that PPC has an active role in determining a faster elimination of the lipids from the treated area.

PCDC can be used successfully to treat localized and small fatty areas of the face. Topical application of PCDC appears better, safer, and more cost effective than liposuction in these specific cases. Additional studies are required to trace the safety profile and appropriate doses of PCDC for treatment of localized fat.

This inventive method and composition for treating fat deposits using PCDC in appropriately selected patients does not induce skin laxity. There is a natural post-treatment appearance without a "surgical look." Surgical or anesthetic risks are eliminated. The method is suitable for patients fearing hospitalization because the inventive method is rapid and home-based, eliminating the need for hospitalization. Patient satisfaction is good. Cosmetic results are good with no skin scars or irregularities. There was less postoperative discomfort than with surgery.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

EXAMPLE 4

A formulation was made comprising the following Phases:

were combined with hot water and mixed at high speed 1500 rpm. Slowly Phase B, C, D and E ingredients were added and mixed until no solid particles remained, i.e. to yield a homogeneous mixture. This mixture was stirred for 30 minutes at 2000 rpm and then cooled to room temperature. The mixture was then added slowly, e.g., dropwise, to a white cream base to result in a white cream/emulsion with continuous high speed stirring. The cream base was cooled to room temperature (about 20° C.) and was stored in a glass beaker away from direct heat and sunlight.

About 1.0 to 2.0 mL of the mixture, depending upon fat area, was applied to an affected skin area to be treated with massage for about 5 to 10 minutes every day for 6 months. Ultrasound images were taken of the affected area before and after 30, 60, 90, 120 and 180 days to monitor quantitative reduction in fat deposition and fat disappearance. There was substantial reduction of fat in the treated areas, e.g. almost 60% reduction in fat in the treated areas.

The present formulation advantageously resulted in reduced burning, irritation and itch, while retaining efficacy to reduce fat deposition.

The invention claimed is:

1. A composition in the form of a cream comprising: deoxycholic acid or salt thereof in a concentration ranging from 0.5% to 30% by wt of the composition, phosphatidylcholine in an amount in the range of 0.1-5% by wt, one or more micelle-forming compounds comprising sodium lauryl sulfate, and an Azelaic-Kojic acid mixture, a hyaluronidase-

| PHASE A | | |
|---|---|---|
| q.s. | water | solvent-diluent |
| 0.75% | sodium lauryl sulfate | emulsifier-detergent |
| 3.0% | Azelaic-Kojic Acid mixture | preservative antimicrobial |
| 3.0% | (L)-carnitine-aminophylline | emollient, preservative, solvent |
| 5.0% | isopropyl alcohol | antiseptic, antimicrobial, solvent, |

| PHASE B | | |
|---|---|---|
| 12.0% | stearic acid | binder, viscosity increasing agent, emulsifier agent |
| 3.0% | glyceryl stearate | viscosity increasing agent, emollient, skin conditioning agent |
| 3.0% | niacin (B3) | emollient, solvent, skin conditioning agent |
| 1.0% | olive oil | moisturizer |
| 4.0% | dimethicone | skin protectant, conditioner |
| 3.5% | MYRJ 52 | surfactant-non-ionic-detergent |
| 4.0% | ethyl alcohol (pure) | antiseptic, antimicrobial, solvent |

| PHASE C | | |
|---|---|---|
| 5.0% | linoleic acid | anti-irritants, emollient skin smoothing agent |
| 0.5% | tocopherol acetate | promotes healing |
| 5.5% | lactic acid | anti-inflammatory, antioxidant, humectant agent |
| 5.0% | niacinamide | (Vitamin B3), anti-redness, moisturizer, antiinflammatory |
| 0.5% | evening primrose oil | treat dry, scaly, or itchy skin, conditions, improves skin texture |

| PHASE D | | |
|---|---|---|
| 0.5% | lecithin-(phospholipon g) | emulsifying |
| 9.0% | sodium deoxycholate | surfactant, emulsifying agent, |
| 0.75% | BRIJ 35 (polyoxyethylene lauryl ether) | surfactant, emulsifier with penetrating effect |
| 0.50% | phenoxyethanol | anti-microbial |

| PHASE E | | |
|---|---|---|
| 0.50% | TEA (triethanolamine) | cleansing agent for skin, anti-microbial |
| 5.0% | Caffeine | prevents excess fat burner |
| 2.5% | Bitter orange extract | reduces cellulite |
| 1.0% | Glycyrrhetinic acid: | reduces subcutaneous fat under the skin |
| 0.25% | Ginkgo biloba: | blocks alpha-receptors; prevents fat build-up |
| 1.0% | Aloe Barbadensis Leaf Extract | fat solubilizer |
| 1.0% | L-Carnitine | fat-burning |
| 0.5% | Nelumbo nucifera Leaf Extract | anti-inflammatory, antioxidant, reduces cellulite |

The following procedure was used to combine the ingredients to form a cream formulation. Phase A ingredients collagenase-artichoke mixture, a (L)-carnitine-aminophylline mixture, thiamine, riboflavin, niacin, pantothenic acid, pyridoxine, and caffeine, combined in a cream base, wherein the composition reduces adipose tissue.

2. The composition of claim 1, wherein the composition comprises sodium deoxycholate.

3. The composition of claim 1, comprising 10% by wt sodium deoxycholate and 5% by weight phosphatidylcholine.

4. A method for non-surgically reducing localized adipose tissue in a patient, the method comprising topically administering to a site at or proximate to adipose tissue, a composition as defined in claim 1, 1-2 times daily for at least 30 days.

5. The method of claim 4, wherein the composition is applied with massage.

6. A composition in the form of a cream or emulsion comprising:

i) as PHASE A, water, 0.75% sodium lauryl sulfate, 3.0% Azelaic-Kojic Acid mixture (50/50), 3.0% artichoke extract, 3.0% (L)-carnitine-aminophylline mixture (50/50) and 5.0% isopropyl alcohol;

ii) as PHASE B, 12% stearic acid, 3.0% glyceryl stearate se, 3.0% niacin, 1.0 olive oil, 4.0% dimethicone, 3.5% 2-hydroxyethyl octadecanoate, and 4.0% ethyl alcohol;

iii) as PHASE C, 5.0% linoleic acid, 0.5% tocopherol acetate, 5.5% lactic acid, 5.0% niacinamide, 0.5% evening primrose oil;

iv) as PHASE D, 0.5% lecithin, 9.0% sodium deoxycholate, and 0.75% polyoxyethylene lauryl ether and 0.50% phenoxyethanol; and vi) as PHASE E, 0.5% triethanolamine and 5.0% caffeine, 2.5% bitter orange extract, 1.0% glycyrrhetinic acid, 0.25% *Ginkgo biloba,* 1.0% Aloe Barbadensis leaf extract, 1.0% L-carnitine and 0.5% *Nelumbo nucifera* leaf extract, combined in order.

7. A method for non-surgically reducing localized adipose tissue in a patient, the method comprising topically administering to a site at or proximate to adipose tissue, a composition as defined in claim 6, 1-2 times daily for at least 30 days.

8. The method of claim 7, wherein the composition is applied with massage.

9. A composition in the form of a cream comprising: deoxycholic acid or salt thereof in a concentration ranging from 0.5% to 30% by wt of the composition; phosphatidylcholine in an amount in the range of 0.1-5% by wt.; one or more micelle-forming compounds selected from sodium lauryl sulfate, polyoxyethylene lauryl ether, 2-hydroxyethyl octadecanoate, olive oil, stearic acid, and evening primrose oil; an Azelaic-Kojic acid mixture; an (L)-carnitine-aminophylline mixture; linoleic acid, tocopherol acetate, niacinamide and triethanolamine, wherein the composition reduces adipose tissue.

10. The composition of claim 9, additionally comprising one or more agents that supplement lipolysis selected from the group consisting of caffeine, bitter orange extract, glycyrrhetinic acid, *Ginkgo biloba*, aloe barbadensis leaf extract, L-carnitine and *Nelumbo nucifera* leaf extract.

11. The composition of claim 10, wherein the deoxycholic acid or salt thereof is in an amount of less than 10% by weight of the composition.

\*  \*  \*  \*  \*